(12) United States Patent
Przybylski et al.

(10) Patent No.: US 7,285,638 B2
(45) Date of Patent: Oct. 23, 2007

(54) METHOD OF OBTAINING BIOLOGICALLY ACTIVE COLLAGEN FROM SKINS OF THE SALMONIDAE FISH

(75) Inventors: Jozef Edward Przybylski, Sopot (PL); Krystyna Siemaszko-Przybylska, Sopot (PL)

(73) Assignee: 3-Helisa Sp. 2 0.0., Gdynia (PL)

( * ) Notice: Subject to any disclaimer, the term of this patent is extended or adjusted under 35 U.S.C. 154(b) by 151 days.

(21) Appl. No.: 10/686,249

(22) Filed: Aug. 9, 2004

(65) Prior Publication Data

US 2006/0135752 A1    Jun. 22, 2006

(30) Foreign Application Priority Data

Oct. 15, 2002    (PL) ...................................... 356650

(51) Int. Cl.
*A61K 38/39*    (2006.01)
*A61K 35/36*    (2006.01)
*A61K 35/60*    (2006.01)
*C07K 1/02*    (2006.01)

(52) U.S. Cl. ...................... 530/356; 530/361; 424/548; 424/572

(58) Field of Classification Search ................ 530/356, 530/361; 424/549, 548, 572
See application file for complete search history.

(56) References Cited

U.S. PATENT DOCUMENTS 5,420,248 A    5/1995    Devictor

| 2003/0004315 A1 | 1/2003 | Macdonald |
| 2003/0032601 A1 | 2/2003 | Kreuter |

FOREIGN PATENT DOCUMENTS

| EP | 0 602 297 | 6/1994 |
| FR | 2 783 836 | 3/2000 |
| FR | 2806415 | 9/2001 |
| PL | 291055 | 7/1991 |
| PL | 312122 | 12/1995 |

*Primary Examiner*—Kathleen Kerr Bragdon
*Assistant Examiner*—Marsha Tsay
(74) *Attorney, Agent, or Firm*—Horst M. Kasper

(57) ABSTRACT

The method of obtaining collagen as above, is characterized by this, that the process of cleaning the skins is done manually using tools made of natural materials such as glass and wood to remove from the skins scales, skills and meat tissue so prepared raw material is placed in a solution of lactic acid of 0.1 to 1.5% concentration, obtaining hydration of collagen contained in the skins. The hydration process is carried out in glass containers, in the temperature from 15 to 20° C., for 24 to 48 hours, conducting a running visual control of the process. Next follows an operation of filtration using silk filters of increasing density. By repeated filtering the cell elements, pigments and remains of the acid solution are removed from collagen. The natural silk filters have a structure similar to the structure of collagen, which prevents damage to the collagen structure.

4 Claims, No Drawings

METHOD OF OBTAINING BIOLOGICALLY ACTIVE COLLAGEN FROM SKINS OF THE SALMONIDAE FISH

CROSS REFERENCE TO RELATED APPLICATIONS

This application is based on a priority application filed on Oct. 15, 2003 in the Republic of Poland and received Polish patent application number 356650.

The subject of the invention is the method of obtaining biologically active collagen from the skins of fresh and salt water species belonging to the salmonidae fish for cosmetic purposes and to assist the functions of tissues and organs of the human body by penetration through the skin to the extracellular space.

Collagen is the most powerful protein of the vertebrate, its molecular mass is 300,000 kD. It is found in all organs and tissues making up their structure in which cell elements are incorporated genetically determining their function. (Strayer's Biochemistry 1). In normal conditions the process of collagen biosynthesis takes place in fibroblasts of the connective tissue and the chondrocytes of the bone in the form of procollagen. It is actively released into the extracellular space.

In the extracellular space the most essential stage of collagen biosynthesis takes place, namely the connecting of the single chains 1, 2 and into a triple helix. The active form of vitamin C and a specific peptidase take part in this process. The triple helix is connected by hydrogen ions of glycine (Strayer's Biochemistry 1). It secures the biological activity of the complicated structure of collagen. The single chain of procollagen is made up of 1000 amino acids, of which ⅓ is glycine. The different kinds of collagen are only differentiated by the constitution of amino acids, which determines its stability according to the needs of the tissues.

The biologically active collagen moves into the extracellular fluid, around all tissues and organs, from where, as a connective tissue protein, it is taken up, regenerating the function of the organs' connective tissue structure, replacing the used up structural protein. During the whole life of the vertebrates a turnover of collagen takes place, similarly to all other proteins. The most stable is the collagen of the bone, where the biosynthesis is regenerated after 300 days (Strayer's Biochemistry). In the bones, the collagen fibers are set in the rhythm of J. S. Bach's Fugue in D major (Strayer's Biochemistry). In the period of physiological ageing as well as in the many pathological congenital and acquired conditions, the processes of destruction of collagen outweigh the processes of its formation. This state inevitably leads to the loss of capacities of cellular and organic functions. (Medic Kelly 10).

The collagen preparations presented here, obtained from animals and fish have shown amino acid identity, not showing any evaluation of biological activity.

According to the current literature (Kelly, Angielski, Strayer), biological activity possesses extracellular protein maintaining three fold helix. It is sensitive to alteration of temperature as well to of all kinds of chemical and synthetic preparations, causing the loss of hydrogen bonds, and in this way transforming into a state called gelatine (Strayer) with the maintained amino acid constitution, percentage containment of low molecular protein, deprived of the physiological activity of collagen.

The discovery solves the problem of elaborating a new way of obtaining a biologically active collagen, replacing the natural collagen, in this way creating new therapeutic possibilities, obtaining a preparation that helps to cure organs affected by illness or old age.

The method of obtaining biologically active collagen from skins of the salmonidae fish is based on the knowledge of stages of its biosynthesis and degradation, also on the physiology of working of the unbroken structure in natural conditions. The method consists, in the first phase, of manual cleaning of the skins with the help of tools made from natural materials, such as glass or wood, to dispose of scales, gills and meat tissue. The material prepared in this way is placed in a 0.1 to 1.5% lactic acid solution, obtaining hydration of the collagen contained in the skins. The hydration is performed in glass containers at the temperatures of 15-20° C., over 24 to 48 hours, maintaining a visual control of the process. Next comes the filtration using natural silk fabric of increasing density, multiple straining causes the separation of pure collagen from elements of the cells, pigments and the remains of the solution of acid. The filters of natural silk have a similar structure to the structure of collagen, which prevents the damage of collagen structure.

The filtering is done about 15 to 20 times through the filters of natural silk, which eliminates from the surface of collagen pigments, remains of the cells, retaining unbounded lactic acid hydrate. The collagen is deprived of the characteristic smell, while the biological activity remains intact.

The product obtained by the discovered method is used transdermally, contains its biological activity which is characteristic only-for an extracellular protein of triple helix. The collagen preparation adheres to the needs of cosmetic recipes, moreover it has additional functions improving the action of organs, tissues, bones, in agreement with its structural destination.

The discovery is presented by an example of its production.

EXAMPLE

The raw material for the production of collagen are the skins of the salmonidae fish—the Polish salmon, Norwegian salmon, Tolpyga.

The initial stage is the preparing of the material for the operation. Every skin is closely inspected to eliminate pathological damage. The damaged skins are immediately removed. Healthy skins are manually cleaned under running water with meticulous removal of scales, gills and meat tissue.

It is important to keep the integrity of the skins. In the preparation of the material glass tools are used. After cleaning the healthy skins are undergoing selection. The darker back parts, the middle parts lightly tinted, and the abdominal parts which are not pigmented. This selection allows obtaining collagen of different resilience to outside pressure. The selected skins are again washed under running water till the water remains clear. Preparing the material is done in a dark location, in agreement with natural conditions. The temperature of the accommodations is kept below 15° C. Glass containers are used of 6l capacity, sterilised, aseptic. The working personnel uses aseptic garments to prevent penetration of bacteria containing enzymes decomposing collagen.

Preparing the Solution for Extraction.

Components are: 90% lactic acid, and distilled water. A 2% solution is prepared by adding 100 ml of lactic acid to 5 litres of water. The 0.5 kg of skins are placed carefully in a 6-litre glass jars and a 1.5% solution of lactic acid with an addition of diluted nipagine in a quantity of 4% of the solution. The whole of so prepared material is kept at the temperature of 15° C. for a period of not less than 24 hours, till the time when the pigment with the elements of cells separates itself from the protein. The obtained collagen has a texture of white jelly.

The last operation is the filtering which must be done in aseptic conditions. Filters of natural silk are used because of the similarity of both proteins—the fibrin of the silk and the collagen. By filtering through different density filters, at least 20 times, the pigment and elements of the cells are separated, the pH is increased to the value of 5.5 to 6.0, and the characteristic smell is eliminated. In every filtering process new filters are used. The obtained product is packed in sterile glass jars hermetically closed. Till the first use it shows stability during one year. The dorsal parts of the skin are of graphite colour as they contain, apart from collagen, dissolved pigment. These are used to restore the nature colour. The middle parts have light graphite colour resistant to temperature above 30° C. The abdominal fragments of the skins—cosmetic collagen, whitish in colour and characterised by quick penetration through the epidermis.

The invention claimed is:

1. A method of extracting biologically active collagen from the skins of the salmonidae fish family comprising:

(a) removing the scales, gills, and meat tissue from the fish skin by utilizing wooden and glass tools in order to obtain a clean skin material;

b) hydrating the skin material in a glass container containing 0.1 to 1.5% lactic acid solution (w/w) at 15° to 20° C. for 24 to 48 hours; and c) repeatedly filtering the hydrated skin solution with natural silk filters that have a similar structure to the biologically active collagen, such that the cell elements, pigments, and remains of the acid solution are removed, and undamaged biologically active collagen is obtained.

2. The method of claim 1, wherein step (c) is repeated 15 to 20 times in order to remove the characteristic fish skin smell without damaging the biological activity of said collagen.

3. The method of claim 1, wherein the silk filters used in step (c) are of increasing density.

4. The method of claim 3, wherein step (c) is repeated 15 to 20 times in order to remove the characteristic fish skin smell without damaging the biological activity of said collagen.

* * * * *